United States Patent
Morita et al.

(10) Patent No.: US 9,637,464 B2
(45) Date of Patent: May 2, 2017

(54) NONIONIC SURFACTANT AND METHOD FOR PRODUCING NONIONIC SURFACTANT

(71) Applicant: NIITAKA CO., LTD., Osaka-shi, Osaka (JP)

(72) Inventors: Masaki Morita, Osaka (JP); Sana Ito, Osaka (JP)

(73) Assignee: Niitaka Co., Ltd., Osaka (JP)

( * ) Notice: Subject to any disclaimer, the term of this patent is extended or adjusted under 35 U.S.C. 154(b) by 0 days.

(21) Appl. No.: 14/784,219

(22) PCT Filed: May 8, 2014

(86) PCT No.: PCT/JP2014/062413
§ 371 (c)(1),
(2) Date: Oct. 13, 2015

(87) PCT Pub. No.: WO2014/203644
PCT Pub. Date: Dec. 24, 2014

(65) Prior Publication Data
US 2016/0075675 A1     Mar. 17, 2016

(30) Foreign Application Priority Data
Jun. 18, 2013   (JP) .................................. 2013-127913

(51) Int. Cl.
| C07D 309/12 | (2006.01) |
| C11D 3/395 | (2006.01) |
| C11D 1/72 | (2006.01) |
| C11D 1/722 | (2006.01) |
| C08G 65/331 | (2006.01) |

(52) U.S. Cl.
CPC ......... C07D 309/12 (2013.01); C08G 65/331 (2013.01); C11D 1/72 (2013.01); C11D 1/722 (2013.01); C11D 3/3956 (2013.01)

(58) Field of Classification Search
CPC .... C07D 309/12; C11D 3/3956; C11D 1/722; C11D 1/72; C08G 65/331
See application file for complete search history.

(56) References Cited

U.S. PATENT DOCUMENTS

| 2,520,611 | A | * | 8/1950 | Roberts | ................... C07C 43/11 252/73 |
| 4,587,365 | A | * | 5/1986 | Anchor | ................... C07C 41/16 568/607 |
| 4,922,029 | A | * | 5/1990 | Birnbach | ........... C08G 65/3344 568/613 |
| 4,988,452 | A |  | 1/1991 | Kinstedt et al. | |
| 5,187,211 | A | * | 2/1993 | Lundy | ....................... C08K 5/06 524/107 |
| 7,241,813 | B2 | * | 7/2007 | Kay | ....................... C08G 65/32 424/400 |

FOREIGN PATENT DOCUMENTS

| JP | 2-043299 | | 2/1990 |
| JP | 2003-516424 | | 5/2003 |
| JP | 2003-516432 | | 5/2003 |
| JP | 2003-516468 | | 5/2003 |
| JP | 2003-516469 | | 5/2003 |
| JP | 2004246276 | A * | 9/2004 |
| JP | 2006-199742 | | 8/2006 |
| JP | 2006-241222 | | 9/2006 |
| WO | 01/41912 | | 6/2001 |
| WO | 01/42408 | | 6/2001 |
| WO | 01/42410 | | 6/2001 |
| WO | 01/42411 | | 6/2001 |
| WO | 2014/073644 | | 5/2014 |

* cited by examiner

*Primary Examiner* — Samantha Shterengarts
*Assistant Examiner* — Matt Mauro
(74) *Attorney, Agent, or Firm* — Hamre, Schumann, Mueller & Larson, P.C.

(57) ABSTRACT

The nonionic surfactant of the present invention has a structure represented by formula (1):

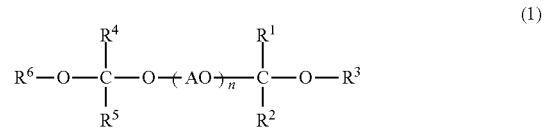

wherein each of $R^1$ and $R^4$ is a hydrogen atom or an alkyl group; each of $R^2$, $R^3$, $R^5$, and $R^6$ is a hydrocarbon group that may contain an ether bond; $R^2$ and $R^3$ may be bonded together to form a cyclic structure, and $R^5$ and $R^6$ may be bonded together to form a cyclic structure; AO represents an oxyalkylene group or oxyalkylene groups that may be the same or different; and n is a number of 1 to 1000 and represents an average addition molar number of the oxyalkylene group or oxyalkylene groups.

7 Claims, 2 Drawing Sheets

NONIONIC SURFACTANT AND METHOD FOR PRODUCING NONIONIC SURFACTANT

TECHNICAL FIELD

The present invention relates to a nonionic surfactant and a method for producing the nonionic surfactant.

BACKGROUND ART

Nonionic surfactants are widely used as materials of detergent compositions for kitchens, bathrooms, and commercial cooking facilities. Examples of nonionic surfactants include higher alcohol EO adducts in which a large number of oxyethylene groups (hereinafter also referred to as EO) are added to a higher alcohol residue.

Detergent compositions may contain a chlorine agent for bleaching stain. Examples of the chlorine agent include salts of acids such as dichloroisocyanuric acid (examples also includes aqueous solutions of these salts) which can generate hypochlorous acid or chlorous acid.

It is known that coexistence of a nonionic surfactant and a chlorine agent in a detergent composition causes deactivation of both the nonionic surfactant and the chlorine agent as a result of a reaction of a terminal hydroxy group of the nonionic surfactant with chlorine of the chlorine agent.

Patent Literature 1 discloses a nonionic surfactant of an end-capped polyalkylene oxide block copolymer which does not bear functional groups that are easily oxidized by a chlorine agent (hypochlorite bleach).

CITATION LIST

Patent Literature

Patent Literature 1: JP 2-43299 A

SUMMARY OF INVENTION

Technical Problem

Patent Literature 1 discloses a nonionic surfactant in which an alkylene oxide is end-capped with a methyl group, resulting in the structure not having a terminal hydroxyl group. According to Patent Literature 1, this nonionic surfactant is more stable in the presence of a chlorine bleach than an uncapped parent molecule.

Patent Literature 1 also discloses a method for methylation of a terminal hydroxyl group at an end of an alkylene oxide moiety by a reaction of a potassium salt of a polyol with dimethyl sulfate in the presence of sodium hydroxide.

The present inventors mixed a chlorine agent with a methyl end-capped nonionic surfactant obtained by the reaction disclosed in Patent Literature 1, and evaluated the chlorine stability of the mixture. As a result, the present inventors found that the chlorine stability of the mixture was not sufficient although it was higher than that of a mixture using non-end-capped nonionic surfactants, and that a portion of the nonionic surfactant reacted with a portion of the chlorine agent, causing decomposition of the chlorine agent.

The present inventors presumed that the insufficient chlorine stability was attributed to the incomplete methylation of a hydroxyl group done by a substitution reaction of a hydroxyl group by a methyl group to leave some residual hydroxy groups.

Dimethyl sulfate is an extremely dangerous compound and thus is preferably not used. The present inventors considered a safer method for end-capping an alkylene oxide moiety to be necessary.

There is another problem. Specifically, the above reaction using dimethyl sulfate requires a purification process because by-products are generated due to the substitution reaction.

The present invention has been made to solve the above problems and aims at providing a nonionic surfactant having higher chlorine stability and a method for safely producing the nonionic surfactant having high chlorine stability.

Solution to Problem

The present inventors conducted intensive studies on the structure of nonionic surfactants having higher chlorine stability and found that if an acetal structure is formed by an addition reaction to a hydroxy group at both ends of the nonionic surfactant molecule, the resulting nonionic surfactant exhibits high chlorine stability particularly under neutral and alkaline conditions. The present invention was thus accomplished.

In other words, a nonionic surfactant of the present invention has a structure represented by formula (1):

(1)

wherein each of $R^1$ and $R^4$ is a hydrogen atom or an alkyl group; each of $R^2$, $R^3$, $R^5$, and $R^6$ is a hydrocarbon group that may contain an ether bond; $R^2$ and $R^3$ may be bonded together to form a cyclic structure, and $R^5$ and $R^6$ may be bonded together to form a cyclic structure; AO represents an oxyalkylene group or oxyalkylene groups that may be the same or different; and n is an integer of 1 to 1000 and represents an average addition molar number of the oxyalkylene group or oxyalkylene groups.

The nonionic surfactant of the present invention has an acetal structure at both ends of the molecule.

The nonionic surfactant of the present invention is described by focusing on one end of the molecule.

The nonionic surfactant of the present invention has an acetal structure (AO—C($R^1$)($R^2$)—O—$R^3$) at one end of the molecule.

One of two oxygen atoms forming the acetal structure is derived from a hydroxy group at the end of a (poly)alkylene glycol molecule.

The acetal structure can be formed by an addition reaction to the hydroxy group at the end of the (poly)alkylene glycol molecule. This addition reaction is quite efficient and thus allows the nonionic surfactant of the present invention to be end-capped to prevent the terminal hydroxy group from remaining.

The nonionic surfactant of the present invention has a similar acetal structure (—O—C($R^4$)($R^5$)—O—$R^6$) at the other end of the molecule.

The acetal structure is unstable under acidic conditions and forms a hydroxy group again, but is stable under neutral and alkaline conditions. In addition, the acetal structure does not react with a chlorine agent. Thus, the nonionic surfactant of the present invention can exhibit high chlorine stability under neutral and alkaline conditions.

Persons skilled in the art who intend to obtain a surfactant having high chlorine stability would usually try to obtain a surfactant having high chlorine stability under both acidic and alkaline conditions. Thus, they would not consider using a surfactant terminated by an acetal structure which is unstable under acidic conditions.

Yet, the present inventors dared to employ a structure terminated by an acetal structure. This resulted in a surfactant having high chlorine stability under neutral and alkaline conditions.

The term "acetal structure" as used herein is a concept that encompasses both an acetal in which $R^1$ or $R^4$ is a hydrogen atom and a ketal in which $R^1$ or $R^4$ is an alkyl group.

If a hydroxy group remains in the nonionic surfactant of the present invention, the hydroxy group may be oxidized into a carboxy group, causing discoloration under alkaline conditions. The nonionic surfactant of the present invention, however, is end-capped not to leave the terminal hydroxy group unreacted, so that such an oxidation reaction would not occur, thus reducing or preventing discoloration.

The nonionic surfactant of the present invention can also achieve low foaming because it is end-capped to prevent the terminal hydroxy group from remaining. Low foaming surfactants are suitable for use as detergents for automatic dishwashers.

The nonionic surfactant of the present invention preferably has a structure represented by formula (2) at at least one end of the molecule:

(2)

The nonionic surfactant of the present invention preferably has a structure represented by formula (3) at at least one end of the molecule:

(3)

wherein m is an integer of 3 or more.

The nonionic surfactant of the present invention preferably has a structure represented by formula (4) at at least one end of the molecule:

(4)

The nonionic surfactant of the present invention preferably has a structure represented by formula (5):

(5)

A method for producing the nonionic surfactant of the present invention includes carrying out an addition reaction to a hydroxy group at both ends of a (poly)alkylene glycol molecule represented by formula (6) to obtain the compound represented by formula (1):

(6)

wherein AO represents an oxyalkylene group or oxyalkylene groups that may be the same or different; and n is an integer of 1 to 1000 and represents an average addition molar number of the oxyalkylene group of the oxyalkylene groups.

In the method for producing the nonionic surfactant of the present invention, a hydroxy group at both ends of the molecule represented by formula (6) is subjected to an addition reaction instead of a substitution reaction so as to end-cap the hydroxy groups with an acetal structure.

Thus, no by-products are generated, and a nonionic surfactant without a hydroxy group at both ends of the molecule can be produced. In addition, a nonionic surfactant having high chlorine stability can be produced without using a dangerous compound such as dimethyl sulfate.

In the method for producing the nonionic surfactant of the present invention, the addition reaction mentioned above is preferably a reaction in which dihydropyran is added to each hydroxy group in the presence of an acid catalyst.

Advantageous Effects of Invention

The nonionic surfactant of the present invention can achieve high chlorine stability under neutral and alkaline conditions.

In addition, the method for producing the nonionic surfactant of the present invention can safely produce a nonionic surfactant having high chlorine stability without generating by-products.

DESCRIPTION OF EMBODIMENTS

The nonionic surfactant of the present invention has a structure represented by formula (1):

wherein each of $R^1$ and $R^4$ is a hydrogen atom or an alkyl group; each of $R^2$, $R^3$, $R^5$, and $R^6$ is a hydrocarbon group that may contain an ether bond; $R^2$ and $R^3$ may be bonded together to form a cyclic structure, and $R^5$ and $R^6$ may be bonded together to form a cyclic structure; AO represents an oxyalkylene group or oxyalkylene groups that may be the same or different; and n is an integer of 1 to 1000 and represents an average addition molar number of the oxyalkylene group or oxyalkylene groups.

The structure represented by formula (1) has an acetal structure at both ends of the molecule.

The acetal structure acts as a protecting group of a hydroxy group. The replacement of a terminal hydroxy group at both ends of the molecule with an acetal structure can prevent deactivation of a chlorine agent due to a reaction of the hydroxy groups with the chlorine agent.

In the nonionic surfactant of the present invention, one of two oxygen atoms forming the acetal structure is derived from a terminal hydroxy group of a (poly)alkylene glycol molecule.

The acetal structure can be formed by an addition reaction to terminal hydroxy groups of the (poly)alkylene glycol molecule. This addition reaction is quite efficient and thus allows the (poly)alkylene glycol molecule to be end-capped without the terminal hydroxy groups unreacted.

Since the acetal structure is stable under neutral and alkaline conditions, it is possible to provide a surfactant that is suitably used in neutral and alkaline detergent compositions.

The acetal structure can be formed by an addition reaction to a terminal hydroxy group. This addition reaction is quite efficient and thus allows the (poly)alkylene glycol molecule to be end-capped to prevent the terminal hydroxy groups from remaining.

In other words, the acetal structure is characterized by "having high stability under neutral and alkaline conditions" and "having no residual hydroxy groups because of the acetal structure formed by an addition reaction".

In addition to the acetal structure, other protecting groups used in the field of organic synthesis (such as methyl, benzyl, acetyl, and trimethylsilyl groups) may be used for protecting hydroxy groups. Use of such protecting groups other than the acetal structure, however, does not satisfy one of the characteristics achieved by use of the acetal structure, i.e., "having high stability under neutral and alkaline conditions" and "having no residual hydroxy groups because of the acetal structure formed by an addition reaction". Thus, these protecting groups are not suitable as structures for end-capping the terminal hydroxy groups. In other words, the surfactant of the present invention bearing terminal hydroxy groups capped with an acetal structure has advantageous effects that cannot be achieved by other surfactants bearing terminal hydroxy groups capped with a different protecting group.

Each of $R^2$, $R^3$, $R^5$, and $R^6$ in formula (1) is a hydrocarbon group that may contain an ether bond. Each of $R^2$ and $R^6$ may be an alkylene group consisting of only carbon and hydrogen atoms, or an alkylene group containing an ether bond. $R^2$ and $R^3$ may be bonded together to form a cyclic structure, and $R^5$ and $R^6$ may be bonded together to form a cyclic structure.

In the nonionic surfactant of the present invention, the structures at both ends of the molecule may be the same or different as long as the surfactant has the structure represented by formula (1). The following description mainly focuses on the structure at one end of the molecule.

If $R^2$ and $R^3$ in the acetal structure in formula (1) are bonded together to form a cyclic structure, the acetal structure is preferably a structure represented by formula (2) below. The structure represented by formula (1) preferably has the structure represented by formula (2) below at at least one end of the molecule.

In the structure represented by formula (2), $R^2$ itself may include a cyclic structure. Examples of the cyclic structure include a cyclohexane ring, a benzene ring, and a naphthalene ring.

If $R^2$ itself includes a cyclic structure, the structure represented by formula (1) may form a fused ring at at least one end of the molecule.

The structure represented by formula (2) is preferably a structure represented by formula (3).

wherein m is an integer of 3 or more.

The structure represented by formula (3) is a structure in which $R^2$ in formula (2) is an alkylene group consisting of only carbon and hydrogen atoms.

The acetal structure represented by formula (3) is preferably a structure represented by formula (4):

The structure represented by formula (4) is a structure in which m is 4 in formula (3).

The structure represented by formula (4) is more preferably a structure in which $R^1$ represents H (tetrahydropyranyl ether).

Tetrahydropyranyl ether is preferred because it is highly stable under neutral and alkaline conditions, and dihydropyran (a raw material of the acetal structure) is easily available at low cost.

This structure can be obtained by the addition of dihydropyran to each hydroxy group in the presence of an acid catalyst as described below.

The term "dihydropyran" as used herein means 3,4-dihydro-2H-pyran (DHP) represented by formula (7) below:

(7)

Examples of the acetal structure represented by formula (2) also include structures represented by formulae (8), (9), and (10) below.

(8)

(9)

(10)

The structure represented by formula (8) is a structure in which $R^2$ is an alkylene group containing an ether bond in formula (2) and can be obtained by the addition of 2,3-dihydro-1,4-dioxin represented by formula (11) below to a hydroxy group in the presence of an acid catalyst.

(11)

The structure represented by formula (9) is a structure in which m is 3 in formula (3) and can be obtained by the addition of 2,3-dihydrofuran represented by formula (12) below to a hydroxy group in the presence of an acid catalyst.

(12)

The structure represented by formula (10) is an example of a structure in which $R^2$ itself has a cyclic structure in formula (2) and in which an end of the molecule having the structure represented by formula (2) forms a fused ring.

This structure can be obtained by the addition of 2,3-benzofuran represented by formula (13) below to a hydroxy group in the presence of an acid catalyst.

(13)

In addition, if the acetal structure in formula (1) includes cyclic structures, a structure represented by formula (5) below in which tetrahydropyranyl ether is formed at both ends of the molecule is preferred.

(5)

This structure can be obtained by the addition of 2 mol of dihydropyran to 1 mol of (poly)alkylene glycol having a hydroxy group at both ends of the molecule, such as polyethylene glycol.

Examples of the acetal structure represented in formula (1) further include, in addition to one in which $R^2$ and $R^3$ are bonded together to form a cyclic structure, one in which $R^2$ and $R^3$ are not bonded together to form a cyclic structure.

If the acetal structure in formula (1) does not include a cyclic structure, a structure in which $R^1$ in formula (1) is an alkyl group is preferred.

$R^1$ may be any straight-chain or branched-chain alkyl group, and examples thereof include methyl, ethyl, propyl, butyl, pentyl, and hexyl groups.

Regardless of whether $R^1$ is an alkyl group or not, each of $R^2$ and $R^3$ in formula (1) above is not particularly limited as long as it is a hydrocarbon group, and examples of $R^2$ and $R^3$ include straight-chain or branched-chain alkyl groups, cyclic hydrocarbon groups, and aromatic hydrocarbon groups.

Specific examples thereof include methyl, ethyl, propyl, butyl, pentyl, hexyl, cyclopentyl, cyclohexyl, phenyl, and benzyl groups.

Each of $R^2$ and $R^3$ may be a hydrocarbon group including an ether bond.

If $R^1$ is an alkyl group and $R^2$ and $R^3$ are not bonded together to form a cyclic structure, a structure represented by formula (14) is preferred. The structure represented by formula (1) preferably includes a structure represented by formula (14) at at least one end of the molecule.

(14)

The structure represented by formula (14) is a structure in which each of $R^1$ and $R^2$ is a methyl group and $R^3$ is an ethyl group in formula (1).

The structure represented by formula (14) is terminated by a 2-ethoxypropyl group and can be obtained by the addition of 2-ethoxy propene to a hydroxy group in the presence of an acid catalyst.

If $R^2$ and $R^3$ are not bonded together to form a cyclic structure in formula (1), examples of preferred terminal structures also include structures represented by formulae (15) to (21) below.

(15)

The structure represented by formula (15) is a structure in which $R^1$ is a methyl group, $R^2$ is an ethyl group, and $R^3$ is a methyl group in formula (1).

This structure can be obtained by the addition of 2-methoxy-1-butene to a hydroxy group in the presence of an acid catalyst.

(16)

The structure represented by formula (16) is a structure in which $R^1$ is a methyl group, $R^2$ is a pentyl group, and $R^3$ is a methyl group in formula (1).

This structure can be obtained by the addition of 2-methoxy-1-heptene to a hydroxy group in the presence of an acid catalyst.

(17)

The structure represented by formula (17) is a structure in which $R^1$ is a methyl group, $R^2$ is a methyl group, and $R^3$ is a cyclohexyl group in formula (1).

This structure can be obtained by the addition of 2-cyclohexyloxy-1-propene to a hydroxy group in the presence of an acid catalyst.

(18)

The structure represented by formula (18) is a structure in which $R^1$ is a methyl group, $R^2$ is a methyl group, and $R^3$ is a phenyl group in formula (1).

This structure can be obtained by the addition of 2-phenoxy-1-propene to a hydroxy group in the presence of an acid catalyst.

(19)

The structure represented by formula (19) is a structure in which each of $R^1$, $R^2$, and $R^3$ is a methyl group in formula (1).

This structure can be obtained by the addition of 2-methoxy propene to a hydroxy group in the presence of an acid catalyst.

(20)

The structure represented by formula (20) is a structure in which each of $R^1$ and $R^2$ is a methyl group, and $R^3$ is a benzyl group in formula (1).

This structure can be obtained by the addition of benzyl isopropenyl ether to a hydroxy group in the presence of an acid catalyst.

(21)

The structure represented by formula (21) is a structure in which $R^1$ is a hydrogen atom, $R^2$ is a methyl group, and $R^3$ is an ethyl group in formula (1).

This structure can be obtained by the addition of ethyl vinyl ether to a hydroxy group in the presence of an acid catalyst.

Examples of AO (oxyalkylene group) in formula (1) include oxyethylene, oxypropylene (hereinafter also referred to as PO), and oxybutylene groups. The nonionic surfactant of the present invention may contain one or more kinds of oxyethylene, oxypropylene, and oxybutylene groups. Repeating units of the oxyethylene, oxypropylene, and oxybutylene groups are also not particularly limited.

Examples of AO having such a structure include —$(PO)_{o1}$-$(EO)_{p1}$—$(PO)_{q1}$— (each of o1, p1, and q1 is an integer of 1 or more) and -$(EO)_{o2}$—$(PO)_{p2}$-$(EO)_{q2}$— (each of o2, p2, and q2 is an integer of 1 or more).

The average addition molar number n of AO in formula (1) is 1 to 1000, preferably 1 to 400, more preferably 3 to 300, still more preferably 5 to 200.

The nonionic surfactant of the present invention is usually a mixture of multiple compounds each having a different addition molar number n of AO. The addition molar number of AO in the nonionic surfactant molecules is an integer. The addition molar number of AO is calculated as the average of the addition molar numbers of AO in each molecule of the nonionic surfactant. This average is thus defined as the average addition molar number.

The nonionic surfactant of the present invention may also be a mixture of multiple compounds containing different kinds of AOs.

The following describes the method for producing the nonionic surfactant of the present invention.

First, a (poly)alkylene glycol having a hydroxy group at both ends of the molecule, which is represented by formula (6), is prepared as a starting material.

(6)

Examples of the (poly)alkylene glycol having a hydroxy group at both ends of the molecule, which is represented by formula (6), include polyethylene glycol, polypropylene glycol, and compounds in which polyethylene glycol and polypropylene glycol are bonded.

Examples of commercially available products include "Pluronic RPE 3110" (trade name, available from BASF Japan, Ltd.) which is polyalkylene glycol in which AO has a structure of HO—$(PO)_{o3}$-$(EO)_{p3}$—$(PO)_{q3}$—H (each of o3, p3, and q3 is an integer of 1 or more) and the molar ratio of EO:PO is 1:9; "Pluronic RPE 2520" (trade name, available from BASF Japan, Ltd.) which is a polyalkylene glycol in which AO has a structure of HO—$(PO)_{o4}$-$(EO)_{p4}$—$(PO)_{q4}$—H (each of o4, p4, and q4 is an integer of 1 or more) and a molar ratio of EO:PO is 2:8; "Pluronic RPE 1740" (trade name, available from BASF Japan, Ltd.) which is a polyalkylene glycol in which AO has a structure of HO—$(PO)_{o5}$-$(EO)_{p5}$—$(PO)_{q5}$—H (each of o5, p5, and q5 is an integer of 1 or more) and the molar ratio of EO:PO is 4:6; "Blaunon P 172" (trade name, available from AOKI OIL INDUSTRIAL CO., LTD.) which is a polyalkylene glycol in which AO has a structure of HO-$(EO)_{o6}$—$(PO)_{p6}$-$(EO)_{q6}$—H (each of o6, p6, and q6 is an integer of 1 or more) and the molar ratio of EO:PO is 2:8; "Blaunon P 174" (trade name, available from AOKI OIL INDUSTRIAL CO., LTD.) which is a polyalkylene glycol in which AO has a structure of HO-$(EO)_{o7}$—$(PO)_{p7}$-$(EO)_{q7}$—H (each of o7, p7, and q7 is an integer of 1 or more) and the molar ratio of EO:PO is 4:6; and "Pluronic PE 6800" (trade name, available from BASF Japan, Ltd.) which is a polyalkylene glycol in which AO has a structure of HO-$(EO)_{o5}$—$(PO)_{p8}$-$(EO)_{q8}$—H (each of o8, p8, and q8 is an integer of 1 or more) and the molar ratio of EO:PO is 8:2.

A hydroxy group at both ends of the molecule of the compound is capped as a result of an addition reaction to the hydroxy groups, whereby the acetal structure represented by formula (1) is obtained.

Specific steps of the addition reaction depend on the acetal structure to be obtained by the addition reaction to the hydroxy groups. For example, the structure represented by formula (4) in which $R^1$ is H (tetrahydropyranyl ether) can be obtained by a reaction of dihydropyran (DHP) with a hydroxy group at both ends of the molecule of the compound in an organic solvent with the presence of an acid catalyst.

Examples of the acid catalyst include p-toluenesulfonic acid, benzenesulfonic acid, methanesulfonic acid, pyridinium p-toluenesulfonate, trifluoromethanesulfonic acid, sulfuric acid, hydrochloric acid, and acidic ion-exchange resin. Among these, p-toluenesulfonic acid is preferred because it is easy to handle and inexpensive.

The organic solvent used for the above reaction may be a typical organic solvent, and examples thereof include dichloromethane, chloroform, acetonitrile, tetrahydrofuran (THF), toluene, chlorobenzene, and methyl tert-butyl ether.

The reaction is terminated by neutralizing the acid catalyst. Any base may be used for the neutralization, and examples thereof include powder of substances such as sodium hydrogen carbonate, sodium hydroxide, and potassium hydroxide, and aqueous solutions thereof.

Reaction conditions can be appropriately determined according to the kind and amount of starting material. Typical reaction conditions are as follows: to a dichloromethane (25 to 100 mL) solution of a (poly)alkylene glycol having a hydroxy group at both ends of the molecule (60 to 70 g) are added dihydropyran in an amount sufficient for a reaction with all the hydroxy groups in the (poly)alkylene glycol (i.e., 2 to 10 times as much as the amount of (poly)alkylene glycol in terms of molar ratio) and p-toluenesulfonic acid (1 to 10 mol %) as an acid catalyst. The reaction mixture is stirred at room temperature for 0.5 to 10 hours (overnight) and then sodium hydrogen carbonate is added to the reaction mixture to terminate the reaction. The mixture is filtered, and the solvent and unreacted dihydropyran are removed in vacuo.

Next, one example of a detergent composition that contains the nonionic surfactant of the present invention is described.

The detergent composition may contain, for example, a nonionic surfactant of the present invention (A) and a chlorine agent (B). In the case of an alkaline detergent composition, the composition may further contain an alkaline agent (C).

The concentration of the nonionic surfactant of the present invention (A) in the detergent composition is not particularly limited, but is preferably 0.1 to 40% by weight, more preferably 0.5 to 25% by weight, still more preferably 0.5 to 10% by weight.

Examples of the chlorine agent (B) include chlorinated isocyanurate salts (such as sodium dichloroisocyanurate and potassium dichloroisocyanurate), trichloroisocyanuric acid, and hypochlorites (such as sodium hypochlorite, potassium hypochlorite, and calcium hypochlorite).

These chlorine agents may be used alone or in combination of two or more thereof.

The nonionic surfactant of the present invention (A) in the detergent composition is terminated not by hydroxy groups but by acetal structures that do not react with the chlorine agent (B). Thus, deactivation of the chlorine agent (B) in the detergent composition is prevented.

The concentration of the chlorine agent (B) in the detergent composition is not particularly limited, but is preferably 0 to 45% by weight as an available chlorine concentration. The concentration of the chlorine agent is preferably 0 to 50% by weight, more preferably 2 to 50% by weight.

If the detergent composition contains several kinds of chlorine agents, the concentration of the chlorine agents is determined as the sum of concentrations of these chlorine agents.

The amount of chlorine agent (B) is preferably the same as or more than the amount of nonionic surfactant of the present invention (A). The ratio of the amount of chlorine agent to the amount of nonionic surfactant (i.e., the amount of chlorine agent/the amount of nonionic surfactant) is preferably 1 to 100, more preferably 1 to 20, still more preferably 1 to 6.

Such a detergent composition containing a relatively large amount of chlorine agent can exhibit excellent bleaching and sterilizing properties.

The alkaline agent (C) may be any alkali metal or any an alkaline-earth metal salt. Preferred examples thereof include sodium hydroxide, potassium hydroxide, sodium carbonate, potassium carbonate, sodium hydrogen carbonate, potassium hydrogen carbonate, sodiummetasilicate, sodium sesquisilicate, sodium orthosilicate, potassium metasilicate, potassium sesquisilicate, and potassium orthosilicate.

These alkaline agents may be hydrates.

Preferred among these is at least one selected from the group consisting of sodium hydroxide, potassium hydroxide, sodium orthosilicate, potassium orthosilicate, sodium metasilicate, potassium metasilicate, and hydrates thereof. Use of these alkaline agents can provide an alkaline detergent having high detergency.

These alkaline agents may be used alone or in combination of two or more thereof.

The concentration of the alkaline agent (C) is not particularly limited, but is preferably 2 to 95% by weight, more preferably 30 to 95% by weight, still more preferably 45 to 95% by weight.

In the case where various alkaline agents are used, the concentration of the alkaline agents is determined as the sum of the concentrations of each alkaline agent.

The pH of the detergent composition is not particularly limited, but is preferably in the neutral to alkaline range in terms of the stability of the terminal acetal structure of the nonionic surfactant of the present invention (A).

In the case of a neutral detergent composition, the pH thereof is preferably 6 or more and lower than 9. In the case of a weak alkaline detergent composition, the pH thereof is preferably 9 or more and lower than 12. In the case of a strong alkaline detergent composition, the pH thereof is preferably 12 or higher.

The pH can be measured by a commercially available pH meter or the like, such as D-21 available from HORIBA, Ltd.

In the above detergent composition, the nonionic surfactant and the chlorine agent can stably coexist in the above pH range. Thus, the detergent composition can exhibit detergent effect owing to the nonionic surfactant, as well as bleaching and sterilizing effects owing to the chlorine agent. In addition, in an alkaline detergent composition containing an alkaline agent, the detergent composition can further exhibit detergent effect against residues such as oil residue owing to the alkaline agent.

The detergent composition of the present invention may contain, if necessary, other components that can be added to a detergent composition, such as a polymer dispersant (D), a chelating agent (E), a solvent/excipient (F), and a solubilizing agent (G). The detergent composition may also contain another surfactant in addition to the nonionic surfactant of the present invention (A).

Examples of the polymer dispersant (D) include polyacrylic acid, polyaconitic acid, polyitaconic acid, polycitraconic acid, polyfumaric acid, polymaleic acid, polymetaconic acid, poly-α-hydroxy acrylic acid, polyvinylphosphonic acid, sulfonated polymaleic acid, maleic anhydride-diisobutylene copolymer, maleic anhydride-styrene copolymer, maleic anhydride-methyl vinyl ether copolymer, maleic anhydride-ethylene copolymer, maleic anhydride-ethylene crosslink copolymer, maleic anhydride-acrylic acid copolymer, maleic anhydride-vinyl acetate copolymer, maleic anhydride-acrylonitrile copolymer, maleic anhydride-acrylic acid ester copolymer, maleic anhydride-butadiene copolymer, maleic anhydride-isoprene copolymer, poly-β-ketocarboxylic acid derived from maleic anhydride and carbon monoxide, itaconic acid-ethylene copolymer, itaconic acid-aconitic acid copolymer, itaconic acid-maleic acid copolymer, itaconic acid-acrylic acid copolymer, malonic acid-methylene copolymer, itaconic acid-fumaric acid copolymer, ethylene glycol-ethylene terephthalate copolymer, vinylpyrrolidone-vinyl acetate copolymer, and metal salts thereof. Suitable examples include sodium polyacrylate (average molecular weight Mw=3,000 to 30,000) and sodium salt of poly(acrylic acid-co-maleic acid) in terms of cost and economy.

Examples of the chelating agent (E) include ethylenediaminetetraacetic acid (EDTA), hydroxyethyl ethylenediaminetriacetic acid (HEDTA), nitrilotriacetic acid (NTA), diethylenetriamine pentaacetic acid (DTPA), 2-phosphonobutane-1,2,4-tricarboxylic acid, ethylenediamine disuccinic acid (EDDS), hydroxyethyliminodiacetic acid (HIDA), glutamic acid diacetate (GLDA), methyl glycine diacetic acid (MGDA), aspartic acid diacetate (ASDA), tripolyphosphate, polyacrylic acid, salts thereof (such as sodium salts and potassium salts), polyaspartic acid-based compounds represented by formula (22) below, iminodisuccinic acid-based compounds represented by formula (23) below, and iminodiacetic acid-based compounds represented by formula (24) below:

in formula (22), each M is the same or different and is —H, —Na, —K, or —NH$_4$; and each of s and t is an integer;

in formula (23), each M is the same or different and is —H, —Na, —K, or —NH$_4$; and in formula (24), each M is the same or different and is —H, —Na, —K, or —NH$_4$.

The concentration of the chelating agent (E) in the detergent composition is not particularly limited, but is preferably 0 to 80% by weight, more preferably 0 to 70% by weight, and still more preferably 15 to 50% by weight.

The solvent (F) may be water or a commonly used organic solvent. The excipient (F) is an extender that is used if the detergent composition is solid, and preferably has a neutral pH. Examples thereof include sodium sulfate.

Examples of the solubilizing agent (G) include xylenesulfonic acid, cumenesulfonic acid, caprylic acid, octanoic acid, salts thereof, and alkyl diphenyl ether disulfonate.

EXAMPLES

The present invention is described in more detail with reference to examples, but the present invention is not limited to these examples.

Example 1

To a dichloromethane solution (50 ml) of polyalkylene glycol (trade name: Pluronic RPE 3110) (80 g) having a hydroxy group at both ends were added dihydropyran (DHP) (6 g) and p-toluenesulfonic acid (1 mol %) as a catalyst. The reaction mixture was stirred at room temperature for 10 hours (overnight) and then sodium hydrogen carbonate was added to the reaction mixture to terminate the reaction. The mixture was filtered, and the solvent and unreacted dihydropyran were removed in vacuo to obtain the target product.

The resulting target product was a nonionic surfactant having an acetal structure at both ends of the polyalkylene glycol molecule, which was obtained by a reaction of a hydroxy group at both ends of the molecule with DHP.

Example 2

A target product was obtained in the same manner as in Example 1 except that a different polyalkylene glycol (trade name: Pluronic RPE 2520) was used instead of the polyalkylene glycol (trade name: Pluronic RPE 3110) and that the amount of DHP was changed.

Example 3

A target product was obtained in the same manner as in Example 1 except that a different polyalkylene glycol (trade name: Pluronic RPE 1740) was used instead of the polyalkylene glycol (trade name: Pluronic RPE 3110) and that the amount of DHP was changed.

Example 4

A target product was obtained in the same manner as in Example 1 except that a different polyalkylene glycol (trade name: Blaunon P 172) was used instead of the polyalkylene glycol (trade name: Pluronic RPE 3110) and that the amount of DHP was changed.

Example 5

A target product was obtained in the same manner as in Example 1 except that a different polyalkylene glycol (trade name: Blaunon P 174) was used instead of the polyalkylene glycol (trade name: Pluronic RPE 3110) and that the amount of DHP was changed.

Example 6

A target product was obtained in the same manner as in Example 2 except that 2,3-dihydrofuran was used instead of dihydropyran (DHP).

Example 7

A target product was obtained in the same manner as in Example 2 except that ethyl vinyl ether was used instead of dihydropyran (DHP).

Example 8

A target product was obtained in the same manner as in Example 1 except that a different polyalkylene glycol (trade name: Pluronic PE 6800) was used instead of the polyalkylene glycol (trade name: Pluronic RPE 3110) and that the amount of DHP was changed.

Comparative Example 1

The polyalkylene glycol (trade name: Pluronic RPE 3110) used to produce the nonionic surfactant of Example 1 was used as the nonionic surfactant of Comparative Example 1.

Comparative Example 2

The polyalkylene glycol (trade name: Pluronic RPE 2520) used to produce the nonionic surfactant of Example 2 was used as the nonionic surfactant of Comparative Example 2.

Comparative Example 3

The polyalkylene glycol (trade name: Pluronic RPE 1740) used to produce the nonionic surfactant of Example 3 was used as the nonionic surfactant of Comparative Example 3.

Comparative Example 4

The polyalkylene glycol (trade name: Blaunon P 172) used to produce the nonionic surfactant of Example 4 was used as the nonionic surfactant of Comparative Example 4.

Comparative Example 5

The polyalkylene glycol (trade name: Blaunon P 174) used to produce the nonionic surfactant of Example 5 was used as the nonionic surfactant of Comparative Example 5.

Comparative Example 6

The polyalkylene glycol (trade name: Pluronic PE 6800) used to produce the nonionic surfactant of Example 8 was used as the nonionic surfactant of Comparative Example 6.

(Chlorine Stability Test)

For the chlorine stability test, detergent compositions each containing one of the nonionic surfactants of Examples 1, 2, 5, 6, 7, and Comparative Examples 1, 2, 5 were prepared. Each detergent composition was evaluated for the chlorine stability.

(Test Formulation 1)

A detergent composition was prepared by mixing 1.5% by weight of the nonionic surfactant of Example 1 or Comparative Example 1, 44% by weight of an aqueous solution of sodium hypochlorite (available chlorine concentration: 12%), 10% by weight of an aqueous solution of sodium hydroxide (concentration: 48% by weight), 30% by weight of a solubilizing agent (an aqueous solution of xylenesulfonate (concentration: 40% by weight)), and 14.5% by weight of water. The detergent composition had a pH of 14.

(Test Formulation 2)

A detergent composition was prepared by mixing 1.3% by weight of the nonionic surfactant of Example 5 or Comparative Example 5, 44% by weight of an aqueous solution of sodium hypochlorite (available chlorine concentration: 12%), 10% by weight of an aqueous solution of sodium hydroxide (concentration: 48% by weight), 10% by weight of an aqueous solution of potassium hydroxide (concentration: 48% by weight), 30% by weight of a solubilizing agent (an aqueous solution of xylenesulfonate (concentration: 40% by weight)), and 4.7% by weight of water. The detergent composition had a pH of 14.

(Test Formulation 3)

A detergent composition was prepared by mixing 3% by weight of the nonionic surfactant of Example 2, 6, 7, or Comparative Example 2, 44% by weight of an aqueous solution of sodium hypochlorite (available chlorine concentration: 12%), 10% by weight of an aqueous solution of sodium hydroxide (concentration: 48% by weight), 10% by weight of an aqueous solution of potassium hydroxide (concentration: 48% by weight), 30% by weight of a solubilizing agent (an aqueous solution of xylenesulfonate (concentration: 40% by weight)), and 3% by weight of water. The detergent composition had a pH of 14.

The available chlorine concentration was measured by iodometric titration described below.

To the detergent composition (about 1 g) were added an aqueous solution of potassium iodide (concentration of about 2% by weight) (50 mL) and acetic acid (10 mL), and then the resulting mixture was stirred vigorously to prepare a test solution. The test solution was titrated with a 0.1 M aqueous solution of sodium thiosulfate, and the endpoint was reached when the brown color of the test solution became colorless. The available chlorine concentration was calculated from the following equation (1), based on the volume of the dropped aqueous solution of sodium thiosulfate at the endpoint of the titration.

Effective chlorine concentration (%)=Amount of dropped aqueous solution of sodium thiosulfate (mL)×0.3546/Amount of detergent composition weighed (g)  (1)

The detergent compositions of Example 1 and Comparative Example 1 were measured for the available chlorine concentration by the above method immediately after preparation of the detergent compositions (0 day) and at day 1, day 4, day 6, day 7, day 8, and day 11 after preparation.

These detergent compositions were stored in an incubator at 45° C. for predetermined days.

Figure 1:
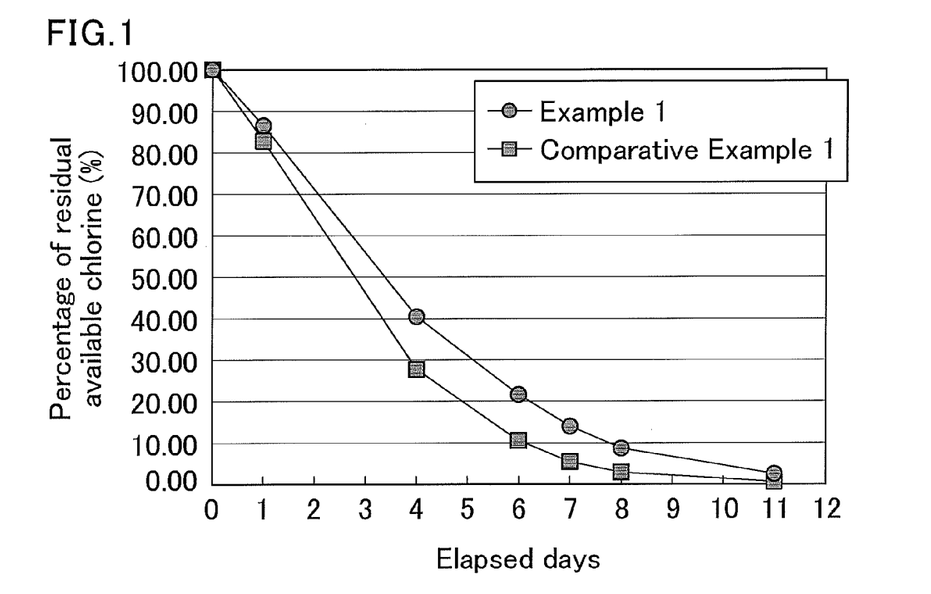
FIG. 1 is a graph showing temporal changes in the percentage of residual available chlorine in a chlorine stability test for Example 1 and Comparative Example 1.

The percentage (%) of the residual available chlorine in each detergent composition was determined as a ratio (%) of the available chlorine concentration at day 1 to day 11 after preparation to the available chlorine concentration immediately after preparation. The available chlorine concentration immediately after preparation was taken as 100(%). Table 1 and FIG. 1 show the results.

TABLE 1

Percentage of residual available chlorine (%)

| | Elapsed days (day) | | | | | |
|---|---|---|---|---|---|---|
| | 0 | 1 | 4 | 6 | 7 | 8 | 11 |
| Example 1 | 100.00 | 86.52 | 40.37 | 21.66 | 13.98 | 8.68 | 2.52 |
| Comparative Example 1 | 100.00 | 82.81 | 27.71 | 10.56 | 5.41 | 2.92 | 0.64 |

The detergent compositions of Example 5 and Comparative Example 5 were measured for the available chlorine concentration by the above method immediately after preparation of the detergent compositions (0 day) and at day 1, day 3, day 6, day 8, and day 10 after preparation.

These detergent compositions were stored in an incubator at 45° C. for predetermined days.

Figure 2:
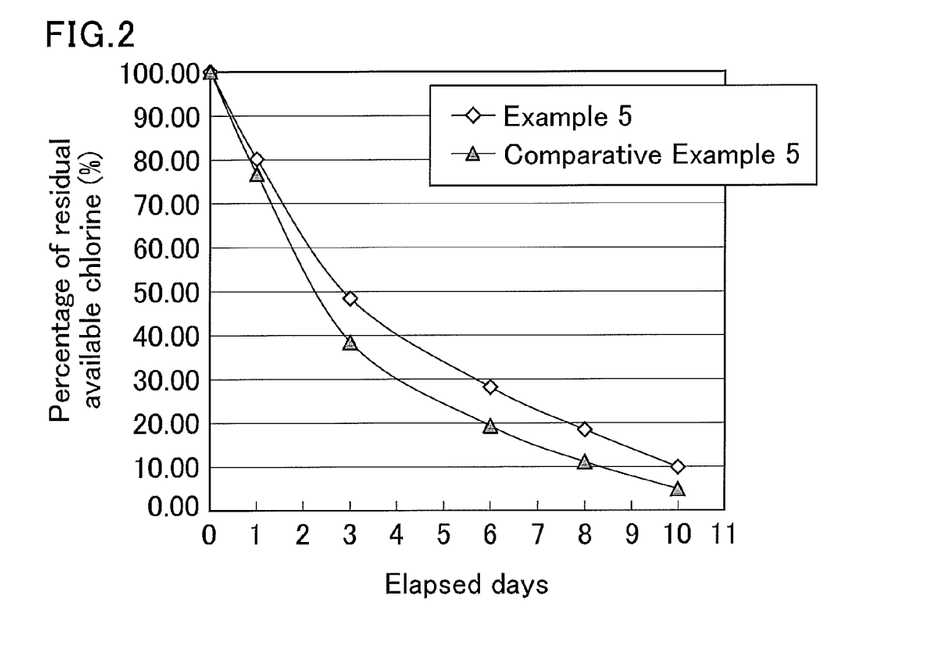
FIG. 2 is a graph showing temporal changes in the percentage of residual available chlorine in a chlorine stability test for Example 5 and Comparative Example 5.

The percentage (%) of the residual available chlorine in each detergent composition was determined as a ratio (%) of the available chlorine concentration at day 1 to day 10 after preparation to the available chlorine concentration immediately after preparation. The available chlorine concentration immediately after preparation was taken as 100(%). Table 2 and FIG. 2 show the results.

TABLE 2

Percentage of residual available chlorine (%)

| | Elapsed days (day) | | | | | |
|---|---|---|---|---|---|---|
| | 0 | 1 | 3 | 6 | 8 | 10 |
| Example 5 | 100.00 | 80.13 | 48.35 | 28.15 | 18.43 | 9.87 |
| Comparative Example 5 | 100.00 | 76.74 | 38.44 | 19.32 | 11.10 | 4.87 |

The detergent compositions of Examples 2, 6, 7 and Comparative Example 2 were measured for the available chlorine concentration by the above method immediately after preparation of the detergent compositions (0 day) and at day 1, day 4, day 6, and day 8 after preparation.

These detergent compositions were stored in an incubator at 45° C. for predetermined days.

Figure 3:
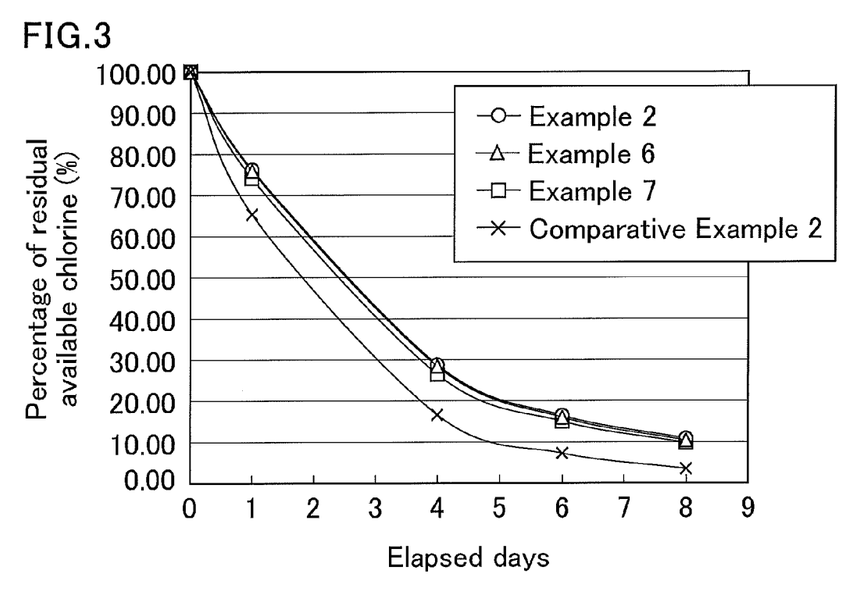
FIG. 3 is a graph showing temporal changes in the percentage of residual available chlorine in a chlorine stability test for Examples 2, 6, 7 and Comparative Example 2.

The percentage (%) of the residual available chlorine in each detergent composition was determined as a ratio (%) of the available chlorine concentration at day 1 to day 8 after preparation to the available chlorine concentration immediately after preparation. The available chlorine concentration immediately after preparation was taken as 100(%). Table 3 and FIG. 3 show the results.

TABLE 3

Percentage of residual available chlorine (%)

| | Elapsed days (day) | | | | |
|---|---|---|---|---|---|
| | 0 | 1 | 4 | 6 | 8 |
| Example 2 | 100.00 | 76.18 | 28.78 | 16.46 | 10.87 |
| Example 6 | 100.00 | 75.85 | 28.42 | 16.01 | 10.41 |
| Example 7 | 100.00 | 74.02 | 26.46 | 15.04 | 9.81 |
| Comparative Example 2 | 100.00 | 65.29 | 16.62 | 7.31 | 3.54 |

According to Tables 1, 2, 3 and FIGS. 1, 2, 3, the detergent compositions containing the nonionic surfactant of Example 1, 2, 5, 6, or 7 have a higher percentage of the residual available chlorine than the detergent compositions containing the nonionic surfactant of Comparative Example 1, 2, or 5.

These results are presumably attributed to the fact that a hydroxy group at both ends of the polyalkylene glycol molecule was capped in each of the nonionic surfactants of Examples 1, 2, 5, 6, and 7.

(Alkali Resistance Test)

For the alkali resistance test, powder of an alkaline agent was applied to the nonionic surfactants of the examples and comparative examples, which were then left to stand for a predetermined time to observe discoloration.

Specifically, each nonionic surfactant (10% by weight) of the examples and comparative examples was mixed with 100% by weight of sodium hydroxide. Then, the resulting mixture was left to stand at 50° C. for 2 hours, and the color of the mixture was visually observed. If the color remained the same, it was evaluated as "no discoloration". If the color changed into brown, it was evaluated as "discoloration to brown". Table 4 shows the results.

TABLE 4

Alkali resistance test

| Sample | Evaluation |
| --- | --- |
| Example 1 | No discoloration |
| Example 2 | No discoloration |
| Example 3 | No discoloration |
| Example 4 | No discoloration |
| Example 5 | No discoloration |
| Example 6 | No discoloration |
| Example 7 | No discoloration |
| Example 8 | No discoloration |
| Comparative Example 1 | Discoloration to brown |
| Comparative Example 2 | Discoloration to brown |
| Comparative Example 3 | Discoloration to brown |
| Comparative Example 4 | Discoloration to brown |
| Comparative Example 5 | Discoloration to brown |
| Comparative Example 6 | Discoloration to brown |

As shown in Table 4, the mixtures of the nonionic surfactants of the examples showed no discoloration. The reason is presumably that a reaction with the alkaline agent did not occur because the nonionic surfactants of the examples were each terminated by an acetal structure at both ends.

In contrast, the mixtures of the nonionic surfactants of the comparative examples showed discoloration to brown. This discoloration is presumably caused by oxidation of the terminal hydroxy groups of the nonionic surfactant of each comparative example into carboxy groups by the alkaline agent.

These results show that the nonionic surfactants of the examples have high alkali resistance and the nonionic surfactants of the comparative examples have low alkali resistance.

(Foaming Test)

The foaming test was performed by the Ross-Miles method (in accordance with JIS K3362). Specifically, each surfactant of Example 5 and Comparative Example 5 was evaluated for foaming properties at 25° C. at 0 minutes and 5 minutes.

A lower foam height indicates lower foaming. In addition, a lower foam height at 5 minutes indicates easily breakable and short-lived foam.

In Example 5, the foam height was 30 mm at 0 minutes, and 3 mm at 5 minutes.

In Comparative Example 5, the foam height was 45 mm at 0 minutes, and 12 mm at 5 minutes.

A comparison of the results between Example 5 and Comparative Example 5 shows that the nonionic surfactant bearing a terminal hydroxy group at both ends capped with an acetal structure achieve low foaming. Low foaming nonionic surfactants are suitable in detergent compositions for automatic dishwashers.

(Detergency Test)

The detergency test was carried out using the nonionic surfactant of Example 1 or 5 or Comparative Example 1 or 5. Specifically, the following components were mixed in such a manner that the concentration of each component was as specified relative to the amount of water in an automatic dishwasher: nonionic surfactant (50 ppm), sodium dichloroisocyanurate (50 ppm), and sodium orthosilicate (0.05% by weight). A washing target was washed in the automatic dishwasher, and the appearance of the resulting washing target was evaluated.

A door type dishwasher (available from HOSHIZAKI ELECTRIC CO., LTD.) was used as the automatic dishwasher under washing conditions at 60° C. for 60 seconds.

The washing target was a glass coated with a combination of stains (a mixture of protein, starch, and grease).

In the detergency test, all of the nonionic surfactants of Examples 1, 5 and Comparative Examples 1, 5 sufficiently washed away the stains. In other words, the nonionic surfactants in which a hydroxy group at both ends of the polyalkylene glycol molecule was capped with an acetal structure had detergency comparable to that of conventional nonionic surfactants bearing uncapped hydroxy groups used in detergent compositions.

The invention claimed is:

1. A nonionic surfactant comprising a structure represented by formula (1):

wherein each of $R^1$ and $R^4$ is a hydrogen atom or an alkyl group; each of $R^2$ and $R^5$ is a hydrocarbon group that optionally contains an ether bond; each of $R^3$ and $R^6$ is a hydrocarbon group that optionally contains an ether bond other than the —O—$R^3$ and $R^6$—O— ether bonds; $R^2$ and $R^3$ may be bonded together to form a cyclic structure, and $R^5$ and $R^6$ may be bonded together to form a cyclic structure; and $(AO)_n$ is $-(PO)_{o1}\text{-}(EO)_{p1}-(PO)_{q1}-$, or $\text{-}(EO)_{o2}-(PO)_{p2}\text{-}(EO)_{q2}-$, where o1, p1, q1, o2, p2, and q2 are integers of at least 1, PO represents oxypropylene, and EO represents oxyethylene.

2. The nonionic surfactant according to claim 1, wherein the nonionic surfactant has a structure represented by formula (2) at at least one end of a molecule:

3. The nonionic surfactant according to claim 1 comprising a structure represented by formula (3) at at least one end of a molecule:

wherein m is an integer of 3 or more.

4. The nonionic surfactant according to claim 1 comprising a structure represented by formula (4) at at least one end of a molecule:

5. The nonionic surfactant according to claim 1 comprising a structure represented by formula (5):

(5)

6. A method for producing the nonionic surfactant according to claim 1 comprising carrying out an addition reaction to a hydroxy group at both ends of a (poly)alkylene glycol molecule represented by formula (6) to obtain a compound represented by formula (1):

(6)

wherein $(AO)_n$ is $-(PO)_{o1}\text{-}(EO)_{p1}-(PO)_{q1}-$, or $-(EO)_{o2}-(PO)_{p2}\text{-}(EO)_{q2}-$, where o1, p1, q1, o2, p2, and q2 are integers of at least 1, PO represents oxypropylene, and EO represents oxyethylene.

7. The method for producing the nonionic surfactant according to claim 6,
wherein the addition reaction is a reaction in which dihydropyran is added to each hydroxy group at the presence of an acid catalyst.

* * * * *